(12) United States Patent
Bencteux et al.

(10) Patent No.: US 9,770,301 B2
(45) Date of Patent: Sep. 26, 2017

(54) MODULE FOR DRIVING A CATHETERIZATION SYSTEM

(71) Applicant: ROBOCATH, Rouen (FR)

(72) Inventors: Philippe Bencteux, St Martin du Vivier (FR); Sébastien Deboeuf, Herblay (FR); Jacques Rignier, Le Mesnil Esnard (FR)

(73) Assignee: Robocath, Rouen (FR)

( * ) Notice: Subject to any disclaimer, the term of this patent is extended or adjusted under 35 U.S.C. 154(b) by 276 days.

(21) Appl. No.: 14/654,359

(22) PCT Filed: Dec. 20, 2013

(86) PCT No.: PCT/FR2013/053214
§ 371 (c)(1),
(2) Date: Jun. 19, 2015

(87) PCT Pub. No.: WO2014/096731
PCT Pub. Date: Jun. 26, 2014

(65) Prior Publication Data
US 2015/0327938 A1  Nov. 19, 2015

(30) Foreign Application Priority Data
Dec. 21, 2012 (FR) .................................... 12 62630

(51) Int. Cl.
*A61B 19/00* (2006.01)
*A61B 34/00* (2016.01)
(Continued)

(52) U.S. Cl.
CPC .......... *A61B 19/2203* (2013.01); *A61B 34/30* (2016.02); *A61B 34/70* (2016.02); *A61B 2034/301* (2016.02); *A61M 25/0113* (2013.01)

(58) Field of Classification Search
CPC .................................................. A61B 19/2203
(Continued)

(56) References Cited

U.S. PATENT DOCUMENTS 5,967,580 A * 10/1999 Rosheim .................... B25J 3/04
294/106
2009/0105645 A1    4/2009 Kidd et al.

FOREIGN PATENT DOCUMENTS

EP      1 442 720 A1    8/2004
EP      1 792 638 A2    6/2007
WO   WO 2005/117596 A2  12/2005

OTHER PUBLICATIONS

International Search Report Application No. PCT/FR2013/053214 report dated May 14, 2014.

* cited by examiner

*Primary Examiner* — David S Luo
(74) *Attorney, Agent, or Firm* — Miller, Matthias & Hull LLP

(57) ABSTRACT

The invention relates to a robotic module for driving a catheterization system, which includes a base and a movable element rotatably mounted, relative to the base, about a rotation axle. The movable element includes: a mounting having a surface for rotating about the axle, the rotating surface comprising an access opening; a transfer system including a fixed part supported by the base and a mobile part for translating the catheter, supported by the mounting, the mobile part having an access opening. The access opening of the mobile part is aligned with the access opening of the rotating surface, regardless of the relative orientation of the mounting and of the base.

20 Claims, 12 Drawing Sheets

(51) Int. Cl.
    *A61M 25/01*    (2006.01)
    *A61B 34/30*    (2016.01)
(58) Field of Classification Search
    USPC .................................................. 318/560, 34
    See application file for complete search history.

US 9,770,301 B2

MODULE FOR DRIVING A CATHETERIZATION SYSTEM

CROSS-REFERENCE TO RELATED APPLICATION

This Application is a 35 USC §371 US National Stage filing of International Application No. PCT/FR2013/053214 filed on Dec. 20, 2013, and claims priority under the Paris Convention to French Patent Application No. 12 62630 filed on Dec. 21, 2012.

FIELD OF THE DISCLOSURE

The present invention relates to robotic modules for driving catheterization systems.

BACKGROUND OF THE DISCLOSURE

Manual insertion of a catheter into a patient is relatively standard surgery. However, as this procedure is performed with X-ray monitoring, the surgeon in charge of the procedure is exposed to substantial radiation when performing such operations on numerous patients.

To reduce the risk to the surgeon, such insertions can be automated using robots. Such automation is complex, because the act of holding the catheter is complex. The catheter is bathed in preservative liquid and must remain sterile. In addition, it should be possible to alternate between rotational and translational movements of the catheter. And of course these robotic systems must be completely reliable.

Recently, a drive system was proposed in U.S. Pat. No. 7,927,310 that manages both the translational and rotational movements of the catheter. The catheter is retained on a plate that rotates relative to a base in order to provide the rotation. The plate itself comprises a mechanism to provide the translation. In addition, there are external motors fixed to the frame, and systems for transferring motion to the catheter. It is preferred not to have embedded motors for reasons concerning power capacity, footprint, and sterility.

However, the problem remains of emergency removal of the catheter from the mechanism. We want to be able to uncouple the catheter from the mechanism as easily as possible when there is an emergency, allowing the surgeon to resume the operation manually. In the above document, because the catheter traverses closed passages, such uncoupling is not allowed for. In addition, the possibility for uncoupling must not adversely affect the normal operation of the robot. In other words, it must not reduce the maneuverability or reliability of the robot.

Also known is WO2005/117,596. This document presents two embodiments. The second embodiment requires embedded motors which, as explained above, is not desirable. The first embodiment provides slotted gear wheels that are independent of each other for the translation and rotation, requiring calculation of the nearest position where the two slots can be aligned, which is complex and dangerous.

The present invention is intended to overcome these disadvantages.

SUMMARY OF THE DISCLOSURE

To this end, the invention provides a robotic module for driving a catheterization system, comprising a base and a movable element mounted to be rotatable, relative to the base, about an axis of rotation extending in a main direction, the movable element comprising:

a mounting extending between first and second ends along the axis of rotation, the mounting having a surface for driving rotation about said axis, said surface for driving rotation comprising an access opening extending in the main direction, a translation control gear, supported by the mounting and rotatable relative to the mounting about an axis extending in said main direction, which when driven generates a translational movement of an elongate flexible medical member along the main direction, a transfer system comprising a fixed part supported by the base and a mobile part supported by the mounting, the fixed part and the mobile part being in a driving relation, the fixed part being drivable by a motor member integral to the base, the mobile part being operatively coupled to the translation control gear such that the translation control gear is in a driving relation with the mobile part, the mobile part having an access opening, characterized in that the access opening of the mobile part extends as a continuity of the access opening of the surface for driving rotation in the main direction, regardless of the relative orientation of the mounting and the base about the axis of rotation.

Indeed, when it must be possible to remove the catheter from the mechanism easily, it is necessary to provide a withdrawal opening in the mechanism. This thus creates a system where the motorization can be placed externally but requires few operations to uncouple the catheter from the mechanism.

This applies to a catheter, but also to any type of suitable elongate flexible medical member, as listed below.

In preferred embodiments of the invention, one or more of the following arrangements may possibly be used:

the mobile part comprises a plurality of gears which are in a meshing relation with each other and with the translation control gear and, regardless of the relative orientation of the mounting and the base, at least one of said gears of the mobile part is in a driving relation with the fixed part, the mobile part comprises a belt supported by the mounting and following a path that defines the access opening of the mobile part, first and second parts are selected among the fixed part and the mobile part, and the first part comprises at least one closed flexible belt having a partially circular path about the axis of rotation, arranged so that, regardless of the relative orientation of the base and the mounting about the main direction, at least a portion of said belt in said path is in an engaging relation with the second part, in order to transmit motion from the motor member to the translation control gear, first and second parts are selected among the fixed part and the mobile part, and the first part comprises at least two members arranged so that, regardless of the relative orientation of the base and the mounting about the main direction, at least one of said members is in an engaging relation with the second part, in order to transmit motion from the motor member to the translation control gear, the first part is the fixed part, and the two members are synchronized, the first part is the fixed part, and the mobile part further comprises at least two members arranged so that, regardless of the relative orientation of the base and the mounting about the main direction, at least one of said members is in an engaging relation with the translation control gear, in order to transmit motion from the motor member to the translation control gear, the first part is the mobile part, and two members are in a meshing relation with the translation control gear, one of the two members is in an indirect meshing relation with the translation control gear via an intermediate gear, one of the two members in an indirect meshing relation with the translation control gear via the other of the two members, the mobile part further comprises at least a third member in a meshing relation with the translation control gear and with the fixed part, the fixed part comprises a closed endless belt comprising a portion following a circular path centered on said axis of rotation.

In another aspect, the invention relates to a robotic module for driving a catheterization system, comprising a base and a movable element mounted to be rotatable, relative to the base, about an axis of rotation extending in a main direction, the movable element comprising:

a mounting extending between first and second ends along the axis of rotation, the mounting having a surface for driving rotation about said axis, said mounting having an access opening extending between its first and second ends along the axis of rotation, a translation control gear, supported by the mounting and rotatable relative to the mounting about an axis extending in said main direction, which when driven generates a translational movement of an elongate flexible medical member along the main direction, the driving module comprising a transfer system comprising a fixed part supported by the base and a mobile part supported by the mounting, the fixed part being drivable by a motor member integral to the base, the mobile part being operatively coupled to the translation control gear such that the translation control gear is in a driving relation with the mobile part, the mobile part having an access opening, characterized in that first and second parts are selected among the fixed part and the mobile part, and in that the first part comprises at least one closed flexible belt having a partially circular path about the axis of rotation, arranged so that, regardless of the relative orientation of the base and the mounting about the main direction, at least a portion of said belt in said path is in an engaging relation with the second part, in order to transmit motion from the motor member to the translation control gear.

In this embodiment, the following may be provided:
a module comprising at least first and second parallel covers, each comprising a groove, the grooves of the first and second covers facing one another, said grooves guiding the belt,
a module wherein the belt is supported by the base,
a module wherein the belt is supported by the mounting,
a module wherein the mounting supports a plurality of rollers that are rotatable relative to the mounting about the main direction, and that guide the belt,
a module wherein the mobile part has an access opening, and
a module wherein the access opening of the mobile part and the access opening of the mounting are joined together, regardless of the relative orientation of the base and the mounting about the main direction.

In another aspect, the invention relates to a robotic module for driving a catheterization system, comprising a base and a movable element that is mounted to be rotatable, relative to the base, about an axis of rotation extending in a main direction, the movable element comprising a mounting extending between first and second ends along the axis of rotation, the mounting having a surface for driving rotation about said axis, said mounting comprising an access opening extending between its first and second ends along the axis of rotation, the movable element further comprising a translation control gear, supported by the mounting and rotatable relative to the mounting about an axis extending in said main direction, which when driven generates a translational movement of an elongate flexible medical member along the main direction, the driving module comprising a transfer system comprising a fixed part supported by the base and a mobile part supported by the mounting, the fixed part being drivable by a motor member integral to the base, the mobile part being operatively coupled to the translation control gear such that the translation control gear is in a driving relation with the mobile part, first and second parts being selected among the fixed part and the mobile part, the first part comprising at least two members arranged so that, regardless of the relative orientation of the base and the mounting about the main direction, at least one of said members is in an engaging relation with the second part, in order to transmit motion from the motor member to the translation control gear.

This aspect reduces the difficulties in reliably driving the elongate flexible medical member during normal operation. With these arrangements, it is certain that one of the two members will transmit the desired motion in a reliable manner, regardless of the position of the withdrawal opening. As a result, a system is obtained that is reliable and that allows effortless removal of the elongate flexible medical member in an emergency.

Other features and advantages of the invention will be apparent from the following description of one of its embodiments, given by way of nonlimiting example with reference to the accompanying drawings.

BRIEF DESCRIPTION OF THE DRAWINGS

In the drawings:

FIGS. 16a and 16b show two variant embodiments of FIG. 8a.

DETAILED DESCRIPTION OF THE DISCLOSURE

In the various figures, the references denote identical or similar elements.

Figure 1:
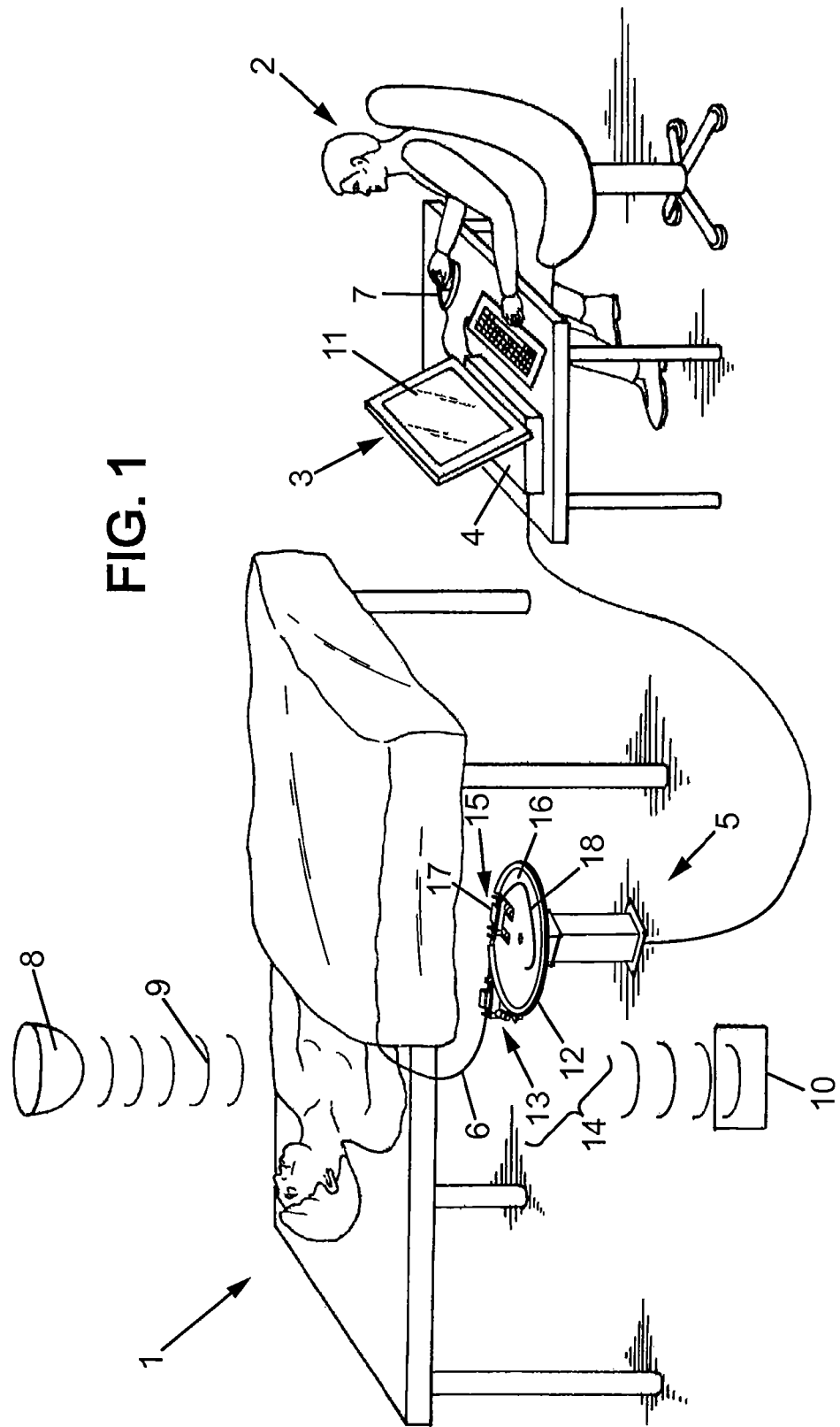
FIG. 1 illustrates an example system for robotic arteriography.

FIG. 1 illustrates an example of a medical system. A patient 1 is lying on an examination table, and the medical staff 2 is performing an automated catheterization. The catheterization is automated via a computerized unit 3 comprising a central processing unit 4 (processor, logic, or other) remotely controlling a robot 5. The robot 5 is able to move an elongate flexible medical member 6 inside the patient 1, under the control of the computerized unit 3. "Elongate flexible medical member" means a flexible member that is longitudinally elongated and that can be inserted into a tubular passage of a patient, particularly an artery or vein of a patient, such as a catheter in the conventional sense of the term, a guide wire guiding such a catheter, an endoscope, an interventional catheter comprising medical equipment such as a balloon, a gripping or surgical tool, etc.

The robot 5 can be controlled by the computerized unit 3 according to a predefined program, or by the medical staff 2 via a user interface 7 such as a mouse, keyboard, joystick, or similar device.

Such catheterization is monitored by imaging, in particular X-ray imaging. An X-ray source 8, 9 may therefore be provided, emitting an X-ray beam toward a patient, as well as an X-ray detector 10 arranged beyond the patient and able to detect transmission of the X-ray beam through the patient. The imaging system can be connected to the computerized unit 3 so that the image obtained by the imaging system is visible on the screen 11 of the computerized unit. Alternatively, the radiographic image is displayed on a dedicated screen. The medical staff 2 can thus control the catheterization while viewing on the screen 11 the position of the elongate flexible medical member within the patient in relation to the various organs of the patient, which allows controlling various movements of the elongate flexible medical member, by means of the robot 5, such as the two main movements which are the longitudinal translation of the elongate flexible medical member in either direction (advancing or withdrawing) and/or the rotation of the elongate flexible medical member about its longitudinal axis (in either direction).

The robot 5 will be described in more detail below. The robot mainly comprises a receptacle 12 wherein the elongate flexible medical member can be contained in a sterile manner. For example, the receptacle 12 is a tube open at one end, which contains the elongate flexible' medical member immersed in a sterile liquid such as normal saline solution. The elongate flexible medical member exits one end of the receptacle 12, and cooperates with a driving module 13 supported by the robot 5 and described in more detail below. The driving module 13 can receive two commands from the computerized unit 3: a command to move translationally along the longitudinal direction of the elongate flexible medical member, and a command to move rotationally about this direction. When appropriate, each command received by the robot comprises a combination of a translation command and a rotation command in different proportions, and a judicious combination of two commands allows ordering a purely translational movement or purely rotational movement of the elongate flexible medical member by simple resolution of mathematical equations.

Note that the robot 5 can be more complex if such is appropriate. In particular, the robot 5 can be used for controlling two medical devices such as an elongate flexible medical member (as described above) and a guide threaded inside the elongate flexible medical member. Thus the robot 5 comprises, in addition to the first system 14 described above, comprising both the container 12 and the driving module 13, a second system 15 comprising a receptacle 16 and a driving module 17 for the medical device contained in the receptacle 16. Similarly, the second system 15 cooperates with the first 14, with the end of the second system 15 connected to the receptacle 12 of the first system 14, and more particularly to the back end of the elongate flexible medical member 6. Thus, the guide 18 can be moved within the elongate flexible medical member 6. Driving module 17 is similar to driving module 13, apart from the adaptation to the diameter of the member to be driven, and will not be specifically described. The robot 5 is controlled by the computerized unit 3 so that the driving module 17 controls the translation of the guide 18 in the longitudinal direction, and the rotation about this direction. The receptacle 16 is, for example, a basin for holding a preservative liquid for storing the guide 18. If necessary, a third system of a similar design (not shown) can be used, nested within the second.

Figure 2:
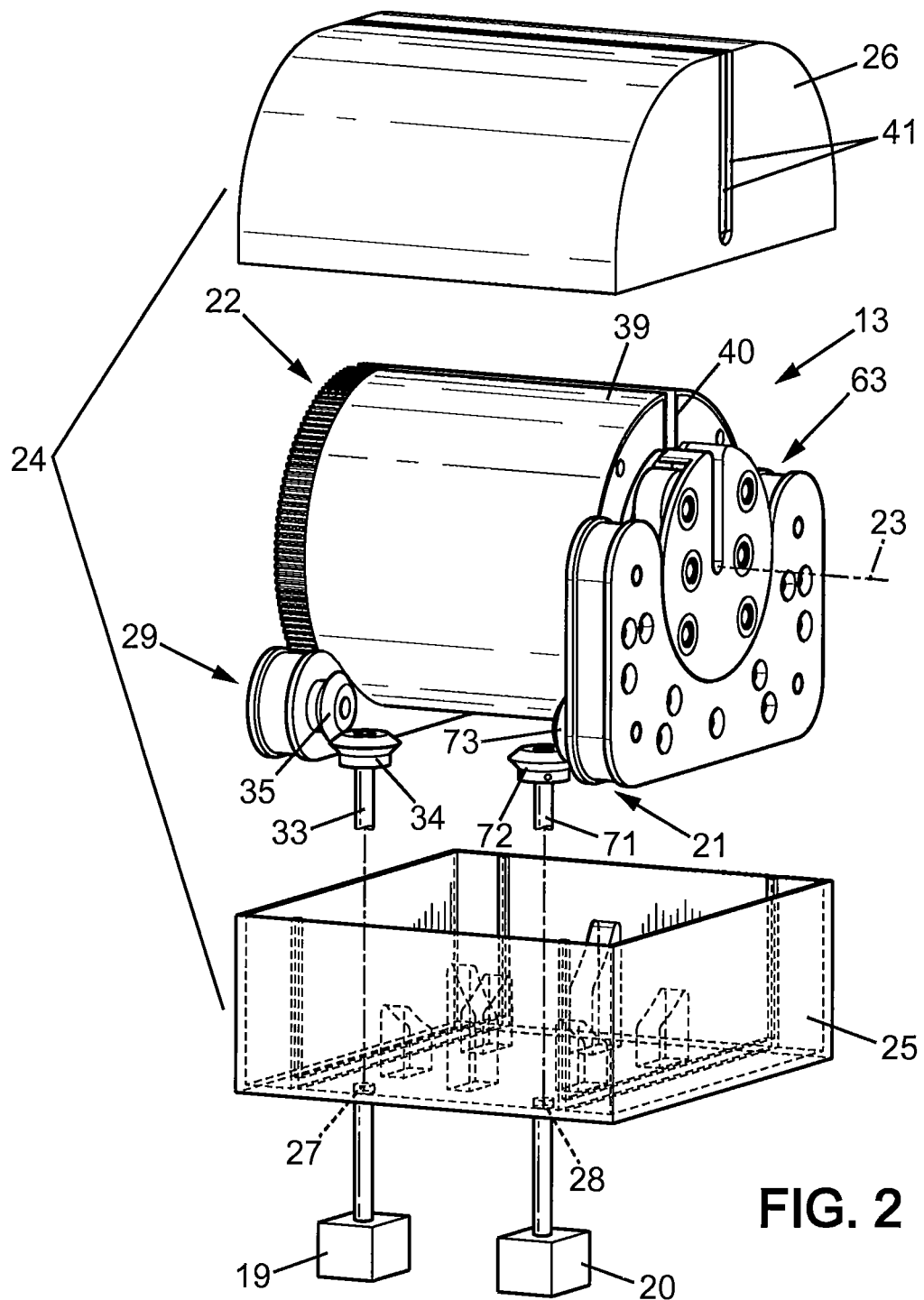
FIG. 2 is an exploded perspective view of a driving module according to a first embodiment.

A first example of a driving module 13 will be described with reference to FIG. 2. A distinctive feature of the driving module 13 is that is has no embedded motor. The motors are fixed and the motions to impart to the elongate flexible medical member are transmitted by a transfer system. Two motors 19 and 20 are thus provided, independently controllable by the computerized unit 3. Motor 19 controls rotation of the elongate flexible medical member 6. Motor 20 controls translation of the elongate flexible medical member 6.

Another distinctive feature of the driving module 13 is that a single module controls both the rotational and translational movements of the elongate flexible medical member. This is achieved in practice by providing a fixed base 21 for the driving module, integral to the motors 19 and 20. The fixed base supports a movable element 22 adapted to rotate about the base 21 about an axis 23 extending in the main direction. In this example, the axis 23 coincides with the longitudinal direction of the elongate flexible medical member to be driven. As will be explained in more detail below in various embodiments, the movable element supports a system 120 for gripping the elongate flexible medical member which possibly may not be driven, in which case the rotation of the movable element relative to the base causes rotation of the elongate flexible medical member about the main direction, or may be driven, resulting in translation of the elongate flexible medical member in the main direction. The problem lies in generating these different movements with fixed motors (not embedded). Embedded motors are preferably avoided because the power issue causes problems (when battery powered, difficult to access in order to change it and could die during a procedure; or when wired, difficult to provide on moving parts). In addition, it is very difficult to reconcile a sterile system with the use of embedded motors, requiring sterilization of these motors after each operation. Fixed motors can more easily be kept behind a sterile barrier, providing a simple seal at the shaft that transfers motion from the motor to the driving module.

The driving module 13 comprises a housing 24 which receives the base 21 and the moving element 22, and provides basic protection from external contaminants. The housing 24 comprises a lower receptacle 25 and an associated cover 26. The receptacle 25 and the cover 26 can be associated (by fitting one inside the other or by some other means) to form a substantially closed space containing the base 21 and the movable element 22. The receptacle 25 comprises two passages 27 and 28 which can respectively be traversed by a rotation control shaft 33 and a translation control shaft 71, respectively connected to the rotation motor 19 and the translation motor 20.

Figure 7:
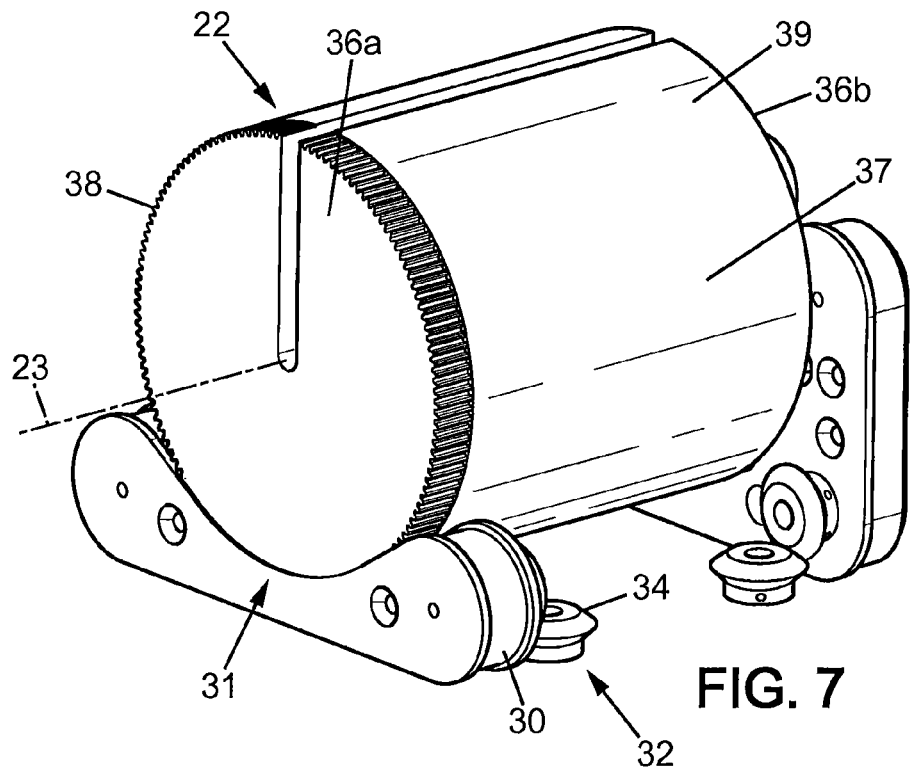
FIG. 7 is a rear perspective view of the system of FIG. 2, FIGS. 8a, 8b, and 8c are front views of the system of FIG. 3, in different driving configurations.

The base 21 contains part of a rotational movement transfer system 29. In particular, the rotational movement transfer system 29 imparts, to the movable element 22, a rotational movement about the axis 23. This system 29 is particularly visible in FIG. 7. In particular, according to this embodiment, the system 29 comprises a closed endless belt 30 movable along a path comprising a portion forming an arc, the center of the arc coinciding with the axis 23. A guide system 31 guides the belt 30 along this path, and will be described in more detail below. A mechanical transfer system 32 is provided for driving the belt 30 along its path. In particular, it may be arranged for example that the end of the rotation control shaft 33 comprises a gear 34 meshing with a gear 35 driving the belt 30. In particular, a mechanical transfer system 32 comprising a right-angle drive transfer may be provided.

The movable element 22 comprises a housing 39 extending between two end faces 36a and 36b along the main direction. The housing 39 comprises an outer peripheral surface 37 defining an almost fully closed right circular cylinder about the axis 23. The outer peripheral surface 37 comprises, for example, a driving right circular cylindrical surface 38 about the axis 23, and cooperating with the belt 30. For this cooperation, it may be arranged for example that the belt 30 has a toothed face and that the driving surface 38 has a complementary toothed surface, the two toothed surfaces being in a driving relation such that movement of the belt 30 causes the housing 39 to rotate about the axis 23.

Referring again to FIG. 2, the housing 39 is not fully closed, and comprises an access opening 40 extending substantially between the two end surfaces 36a and 36b. In particular, the access opening 40 extends continuously along the main direction. In particular, the access opening also extends along the driving surface 38. The access opening 40 is large enough to allow insertion or removal of an elongate flexible medical member 6 in the housing 39. In addition, two lips 41 of elastomer may be provided that close off the access opening 40, preventing contaminants from entering said access opening but deformable to allow inserting or removing an elongate flexible medical member between them.

Figure 5:
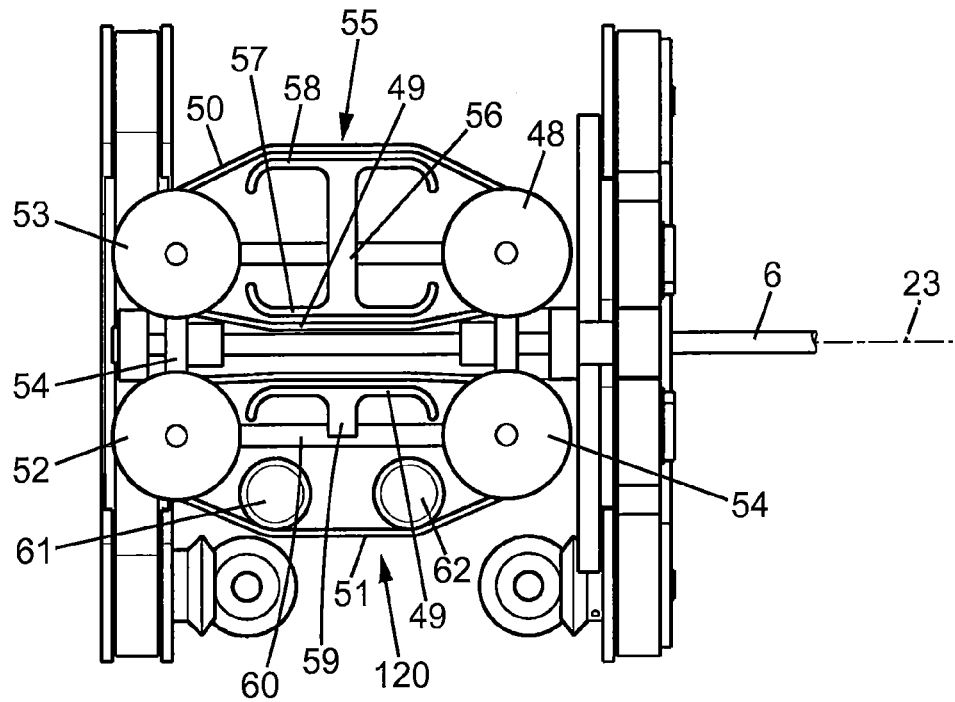
FIG. 5 is a top view of the system of FIG. 3.
Figure 6:
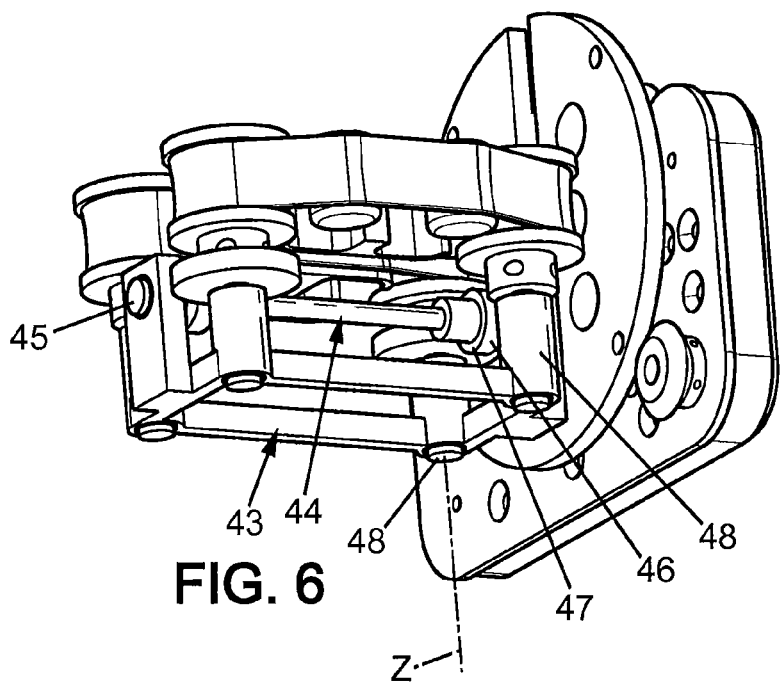
FIG. 6 is a bottom perspective view of the system of FIG. 3.

Referring now to FIGS. 5 and 6, we shall describe a translation driving system for the elongate flexible medical member 6. The translation driving system comprises a frame 43 fixed to the housing 39. The frame supports a drive shaft 44 via an end bearing 45 and a second end bearing 46 at the opposite end. The drive shaft 44 extends along the main direction substantially parallel to the axis 23 but offset relative thereto in a transverse direction. It extends between a first end turning within end bearing 45, and a second end protruding beyond bearing 46. In addition, the shaft 44 comprises at least one gear 47 concentric with the axis of the shaft 44, for rotating a translation driving member 48 of the elongate flexible medical member. In this example, the translation driving member 48 of the elongate flexible medical member is a shaft mounted on the frame 43 so as to be rotatable about an axis normal to the main direction, meaning the transverse direction. The translation driving member 48 is operatively coupled to an application surface 49 placed in contact with the elongate flexible medical member 6, such that the rotation of the translation driving member 48 about the transverse direction drives the elongate flexible medical member 6 translationally along the axis 23. In the example shown, there are in particular application surfaces 49 which are supported by belts 50 and 51 arranged one on each side of the elongate flexible medical member 6. The belts 50 and 51 are endless belts driven by the rotation of a respective translation driving member 48, 52. For example, a translation driving member 48 is used as described above to drive belt 50, and a similar member 52 is used to drive belt 51. Member 52 is arranged diagonally to member 48 in a rectangle whose other two vertices contain driven pulleys 53 and 54. Thus, on one side translation driving member 48 and driven pulley 53 receive belt 50. On the other side, driving member 52 and driven pulley 54 receive belt 51. Translation driving member 52 also cooperates with the shaft 44, via a transfer gear 54 supported by the shaft 44.

Alternatively, a system of belts is not necessarily used and there is direct use of the member 48 and a counter-member which are arranged one on each side of the elongate flexible medical member 6 in order to drive the translation.

The main direction 23 was described above as being that of the translation driving axis of the elongate flexible medical member. The transverse direction was defined as the direction of the axis between the level of the shaft 44 and the level of the elongate flexible medical member 6. A third direction can be defined, the lateral direction, forming a trihedron with the two other directions. A lateral movement system 55 may be provided for the elongate flexible medical member 6. For example, a spacer 56 is provided that can be moved laterally and which comprises a contact surface 57 cooperating with an inner face of the belt 49. Moving the spacer 56 in the lateral direction will laterally move the application surface 49 of the belt 50. This clamps the elongate flexible medical member 6 between the two belts and/or shifts the axis along which the elongate flexible medical member extends between the application surfaces relative to axis 23 (while keeping these axes parallel) in order to improve the driving in rotation.

The spacer 56 also comprises a tensioning surface 58 intended for tensioning the belt 50. The spacer 56 comprises, for example, in the lateral direction, a front face providing the contact surface 57, and a rear face opposite the front face. The rear face provides the tensioning surface 58, which cooperates with the belt on the return side. Thus, regardless of the lateral offset imposed by the spacer 56 within the dedicated interval, the belt remains tensioned.

On the side opposite the spacer 56 relative to the elongate flexible medical member 6, the lateral movement system 55 comprises a pusher 59. The pusher 59 may be movable in the lateral direction. The pusher 59 comprises contact surface 60 opposite contact surface 57. The elongate flexible medical member 6 is grasped by the belts 50 and 51 between these two contact surfaces 57 and 60. The lateral offset of the axis of the elongate flexible medical member, imposed by the spacer 56, can cause displacement of the pusher 59 in the lateral direction via the elongate flexible medical member, against a biasing means (not shown).

On this same opposite side, two tensioning pulleys 61 and 62 are provided which, together with the contact surface 60, tension the belt 51. The two tensioning pulleys 61 and 62 are mounted to be rotatable about the transverse direction relative to the frame 43.

Thus, as one can see from the above description, installing the elongate flexible medical member 6 within the movable element comprises placing the elongate flexible medical member 6 between the two belts 50 and 51. The clamping of the elongate flexible medical member 6, and the lateral offset of the axis of the elongate flexible medical member relative to axis 23, are obtained by adjusting the lateral movement system, meaning by adjusting the lateral position of the spacer 56, via an adjustment system that is not shown (for example manually before the operation).

Once the elongate flexible medical member 6 is in position and clamped, movement of the elongate flexible medical member along the axis 23 is controlled by simple rotation of the drive shaft 44. Rotation of the drive shaft 44 relative to the frame 43 about its axis, parallel to axis 23, causes rotation of at least rotation driving member 48 about its own axis (transverse axis) due to meshing. In practice, in the present case, rotation of the drive shaft 44 relative to the frame 43 about its axis, parallel to axis 23, also causes rotation of rotation driving member 52 about its own axis (transverse axis) due to meshing. Rotation driving member 48 drives belt 50, the application surface thereof then being subjected, at the interaction with the elongate flexible medical member 6, to a translational movement parallel to axis 23. Rotation driving member 52 drives belt 51, the application surface thereof then being subjected, at the interaction with the elongate flexible medical member 6, to a translational movement parallel to axis 23. These two movements are generated in the same translational direction for the application surfaces (in other words, in opposite directions of rotation of the two belts). The movement of the belts drives in translation the elongate flexible medical member.

To generate a translational movement of the elongate flexible medical member 6, it is therefore sufficient to rotate the shaft 44.

However, as the shaft 44 describes a rotation about the axis 23 due to the rotation of the movable element about this axis, while the translation motor 20 remains fixed relative to the frame, a transfer system 63 needs to be provided which always connects the shaft 44 to the motor 20, regardless of the position of the movable element 22 relative to this direction. The transfer system 63 comprises a fixed part 64 supported by the base 21, and a mobile part 65 supported by the movable element 22. A first exemplary embodiment will be given with reference to FIGS. 2 and 3.

According to this first embodiment, the fixed part 64 comprises a belt 66 which is guided along a closed continuous path. A guide 67 is provided for the belt, which will be described in detail below with reference to FIG. 9.

Figure 4:
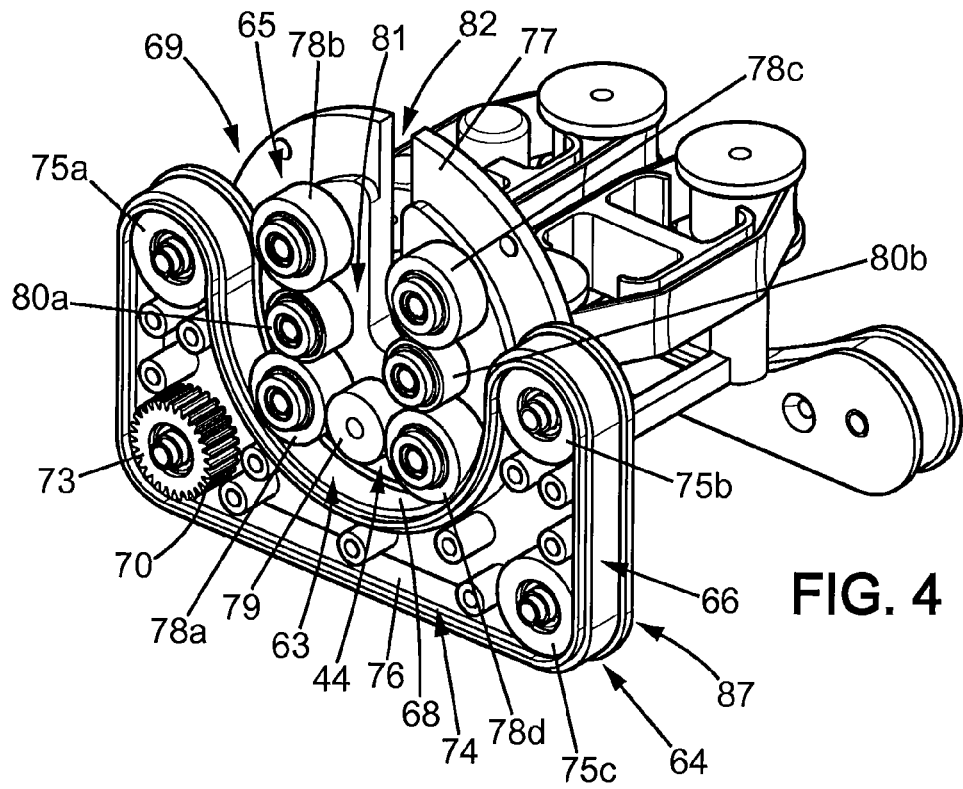
FIG. 4 is a partial view of the system of FIG. 3.

The belt 66 has a portion 68 forming an arc centered on the axis 23. This arc portion 68 has a minimum central angle, which will be explained in more detail below, and a maximum central angle which is strictly less than 360°. In particular, the belt 66 defines an access opening 69 that is large enough to allow the passage of the elongate flexible medical member 6. In the particular example represented, the arc portion 68 of the belt 66 has a central angle of about 180°. The belt 66 also has a driving portion 70. The driving portion 70 receives the drive command from the translation motor 20. For example, as represented in FIG. 2, the fixed part 64 comprises a shaft 71 connected to motor 20, traversing passage 28, and rotating a gear 72 about the vertical axis. Said gear cooperates by conical meshing with a gear 73 having an axis parallel to axis 23. This gear 73 cooperates with the driving portion 70 of the belt as shown in FIG. 4.

The fixed part 64 comprises a set of pulleys adapted to guide the belt 66 so that it moves along a path 74 comprising both the driving portion 70 and the arc portion 68. For example, pulleys 75a, 75b, 75c are provided having parallel axes and arranged to form a rectangle with the gear 73. The path 74 includes three sides of the rectangle, and the arc portion 68 is provided in place of the fourth side. Note that the inner face 76 of the belt 66 is designed to cooperate with the gear 73 to transmit motion via matching shapes, meshing, or other.

The mobile part 65 comprises a support disc 77 integral to the frame 43. The support disk 77, the frame 43, and any other fixed part, in particular the housing 39, of the movable element 22 forming a frame assembly are generally referred to as a "mounting" 121. The support disc 77 supports a plurality of gears 78a, 78b, 78c, and 78d. These gears 78a-d are each mounted relative to the support disc 77 so as to be rotatable about an axis parallel to the main direction. In addition, these gears 78a-78d are arranged in a circle centered on the axis 23 (therefore concentric with the arc portion 68 of the belt 66). The radius of this circle is smaller than the radius of the arc portion 68 of the belt 66. Each gear 78a-d has its own radius, such that the sum of the radius of the circle and of the radius of the gear 78a-d corresponds to the radius of the arc portion 68 of the belt 66.

Furthermore, each gear 78a-d is in a meshing relation with the shaft 44 passing through the support disc 77. For example, a direct meshing relation may be provided, as is the case for the two gears 78a and 78d which are in direct contact with the head 79 of the shaft 44. There may also be an indirect meshing relation, as is the case for the two gears 78b and 78c which are in contact with the head 79 of the shaft 44 via the two gears 78a and 78d.

A system may also be provided for transferring motion between the "indirect" gears 78b and 78c and the "direct" gears 78a and 78d, so that all they rotate in the same direction. There can thus be an intermediate gear 80a provided between gears 78a and 78b and an intermediate gear 80b provided between gears 78c and 78d.

Thus, the support disc 77 supports a mechanized system 78a-78d, 80a-80b, which has an access opening 81 aligned with an access opening 82 of the support disc 77. In the present case, the mechanized system has gears arranged in a general U shape, the open side of the U defining the access opening 81. A first arm of the U comprises aligned gears 78a, 80a, and 78b. A second arm of the U comprises aligned gears 78d, 80b, and 78c. Gears 78a and 78d are arranged one on either side of the head 76 of the shaft 44 to form the base of the U.

In the position represented in FIG. 4, the gears 78a and 78d are engaged with the belt 66 in the arc portion 68 of the belt. In this position, to drive in translation the elongate flexible medical member 6 along the axis 23, gear 73 drives the belt 66. The belt 66 rotates gears 78a and 78d about their own axis relative to the support disc 77 (assuming for simplicity that the support disc 77 is unmoving during this operation). Gears 78a and 78d rotate the shaft 44 by means of the head 79. Rotation of the shaft 44 causes translation of the elongate flexible medical member by the mechanism described above.

Figure 3:
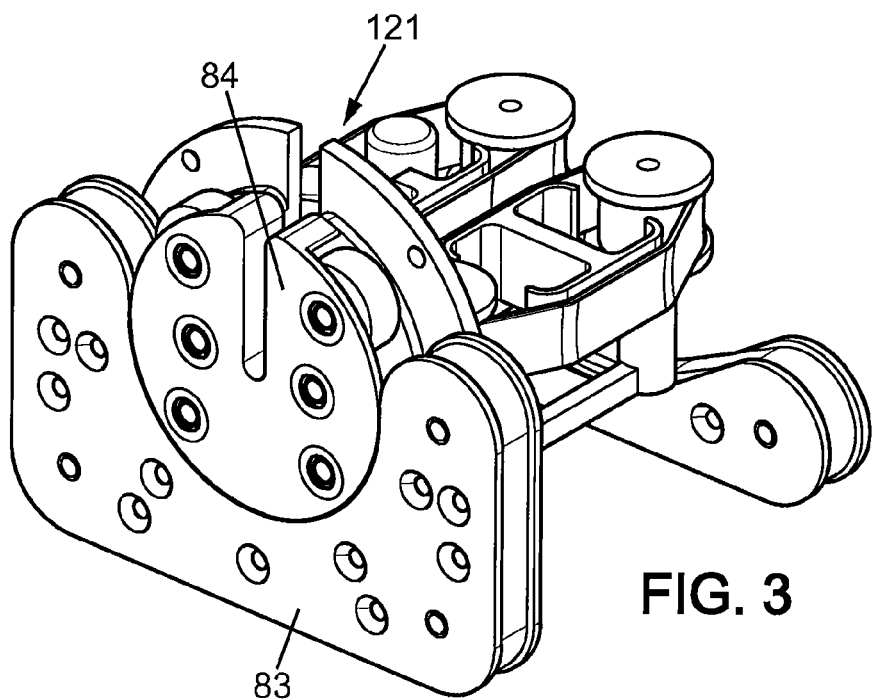
FIG. 3 is a partial view of the system of FIG. 2.

As shown in FIG. 3, in actual practice the various mechanisms are hidden and guided by covers 83 and 84 for the fixed part and mobile part respectively. The covers have the same access openings as described above, and define bearings for the shafts of the various gears.

Figure 9:
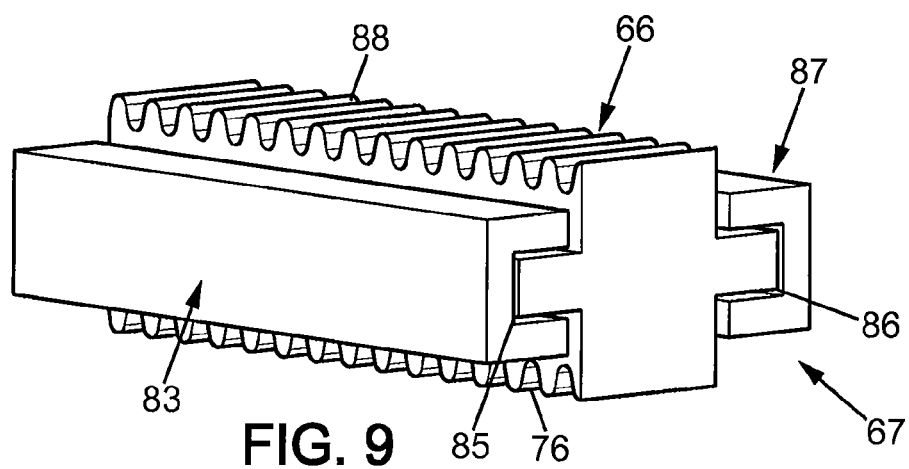
FIG. 9 is a detailed perspective view of driving the belts of the system of FIG. 2.

As shown in FIG. 9, the belt 66 is guided by a guide system which comprises a groove 85 formed in the cover 83, and a similar groove 86 formed in a plate 87 opposite the cover 83. A similar system may be provided for any of the belts of the various embodiments described herein.

As the inner face 76 of the belt is designed to mesh with gear 73, and the opposite outer face 88 is designed to mesh with gears 78a-d, each is shaped for such meshing, for example by being provided with teeth that fit with the teeth of the various gears.

Figure 8A:
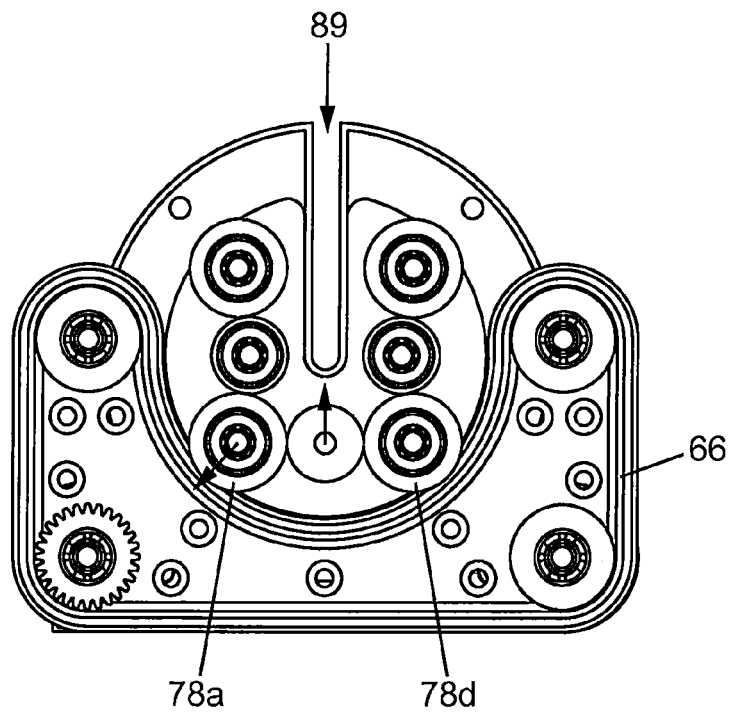

FIG. 8a shows an initial position of the driving module. During a preparatory phase, the single access opening 89, formed by the various aligned access openings 81, 82, 40, allows insertion of the elongate flexible medical member into the module, in particular between belts 50 and 51.

To generate a pure translational movement, the rotation motor 19 is locked. The translation motor 20 is controlled to generate movement of belt 66 along its path. The arc portion 68 causes gears 78a and 78d to rotate about their axis, which drives the translation of the elongate flexible medical member along axis 23. The elongate flexible medical member 6 can be withdrawn at any time via the access openings.

To generate a rotational movement, the rotation motor 19 rotates belt 30 which causes the movable element 22 to rotate about axis 23. During this movement, gears 78a and 78d roll on belt 66 until one of the gears, here gear 78d, exits the arc portion 68. In addition, it may be desirable to prevent translational movement of the elongate flexible medical member when ordering the rotation. In this case, action is taken so that the relative orientations of the shaft 44 and the elongate flexible medical member 6 within the movable element remain unchanged (meaning that the shaft 44 does not rotate relative to the frame 43). This can be achieved by controlling the translation motor so that the belt 66 travels a corresponding distance to prevent rotation of gears 78a-d relative to the support disc 77.

Figure 8B:
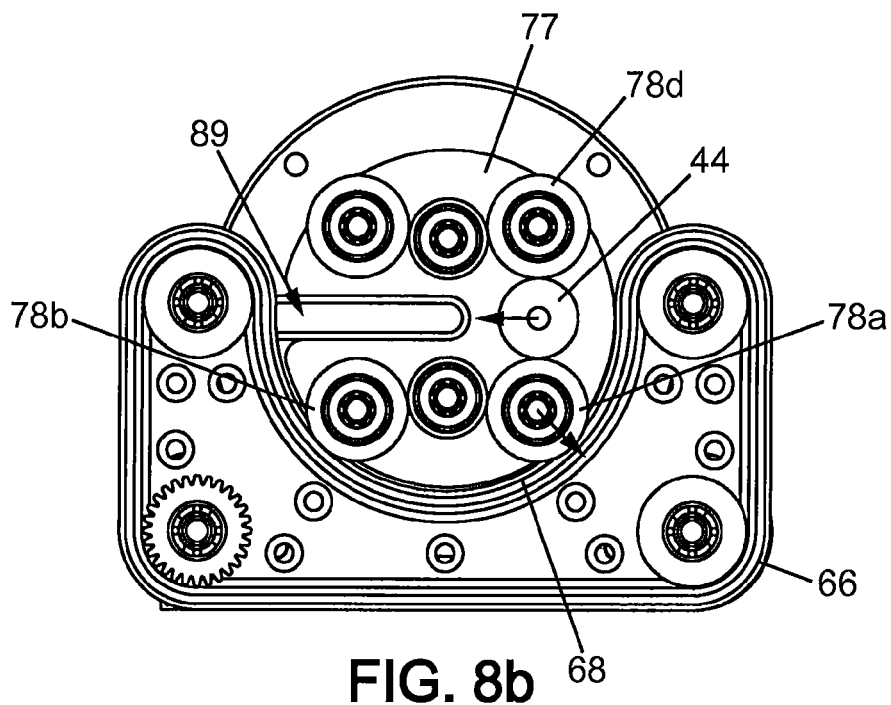
Figure 8C:
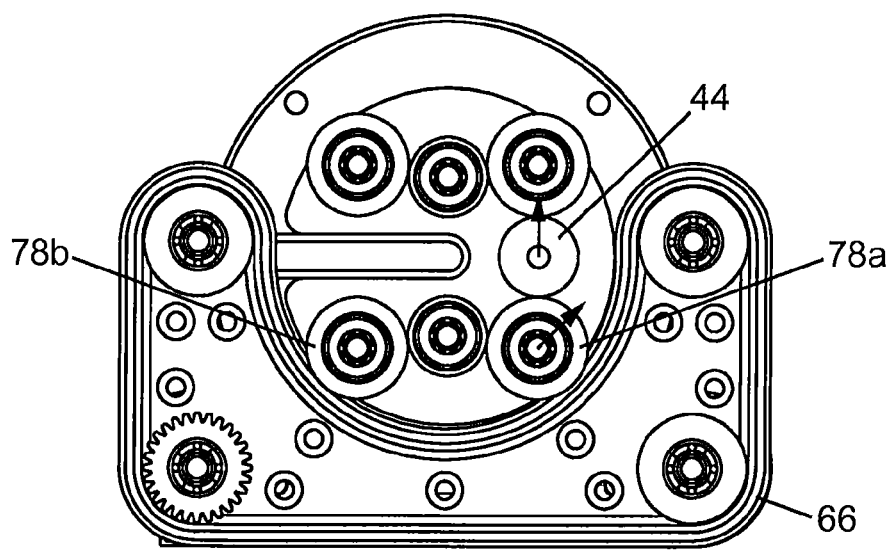

This is particularly clear when comparing FIGS. 8a and 8b, where arrows have been added to the various moving components to illustrate their orientations relative to the different positions.

Thus, if the operator wants to obtain a pure rotational movement of the elongate flexible member medical 6, the two motors 19 and 20 are controlled in predetermined ratios.

During rotation of the movable element 22, the elongate flexible medical member 6 remains captured between belts 50 and 51 from which it receives the rotational motion imparted to the movable element.

Of course, it could be arranged to order a simultaneous translation and rotation of the elongate flexible member medical 6, in which case solely the rotation motor 19 may be controlled, or the two motors 19 and 20 may be controlled according to a ratio other than the predetermined ratio for pure rotation.

As can be seen in FIG. 8b, in this position it is not possible to withdraw the elongate flexible medical member 6 via the access opening 89, because the opening is obstructed by the belt 66 of the fixed part. However, there remains only one access opening 89. To remove the elongate flexible medical member 6 from the module when in this position, the rotation motor is controlled to achieve a rotational movement in the appropriate direction, for example towards the position of FIG. 8a. If wanting to withdraw the elongate flexible medical member 6 from the module with no translational movement of the member within the patient, the translation motor is controlled according to the predetermined ratio for generating the pure rotational movement.

If, in the position of FIG. 8b, translation of the elongate flexible medical member 6 is desired, the rotation motor 19 is locked and the translation motor 20 is controlled as explained above. In the position represented, the arc portion 68 of the belt 66 causes rotation of gear 78a and gear 78b, but no longer that of gear 78d as above. Regardless of the relative orientation of the movable element 22 and the base 21, at least one gear 78a-d is in a driving relation with the arc portion 68 of the belt 66. This property defines the minimum central angle of the arc portion 68 of the belt 66, based on the number and arrangement of gears 78a-78d. In the square configuration shown, the minimum central angle of the arc portion 68 of the belt 66 is at least 90°. In the example, 180° is provided for clarity.

Figure 16A:
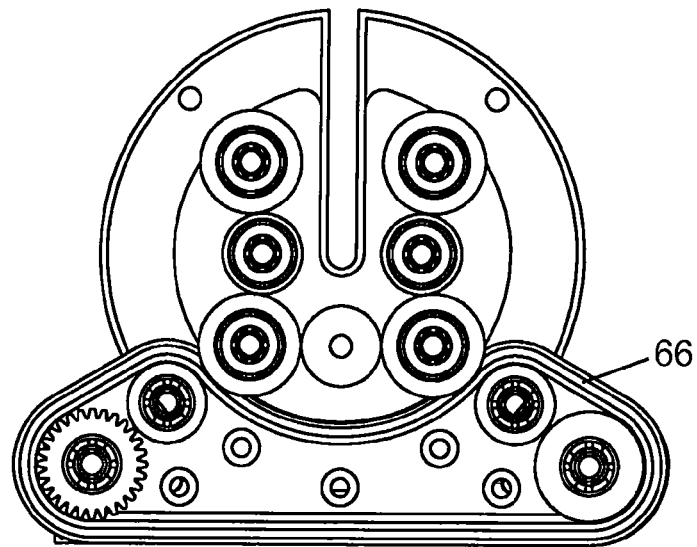
Figure 16B:
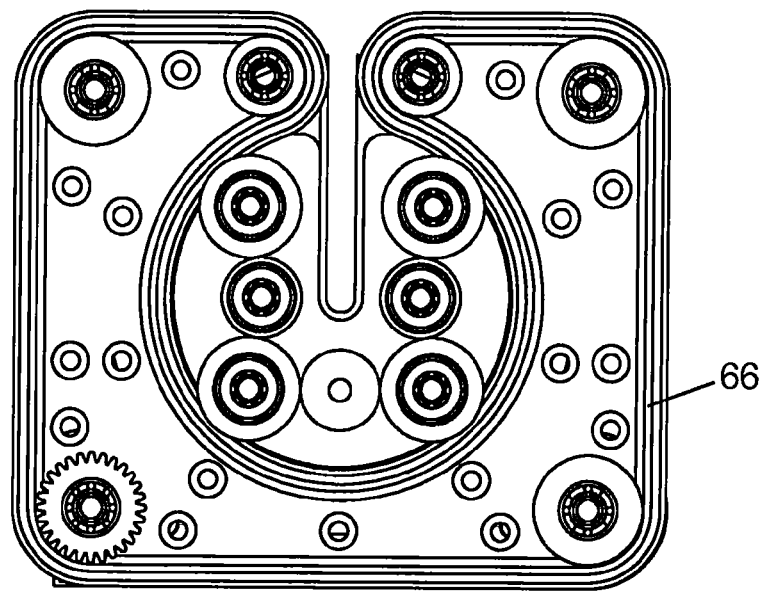

FIGS. 16a and 16b represent two alternative embodiments where the paths of the belt 66 respectively tend towards a minimum and maximum central angle for this configuration.

Figure 10:
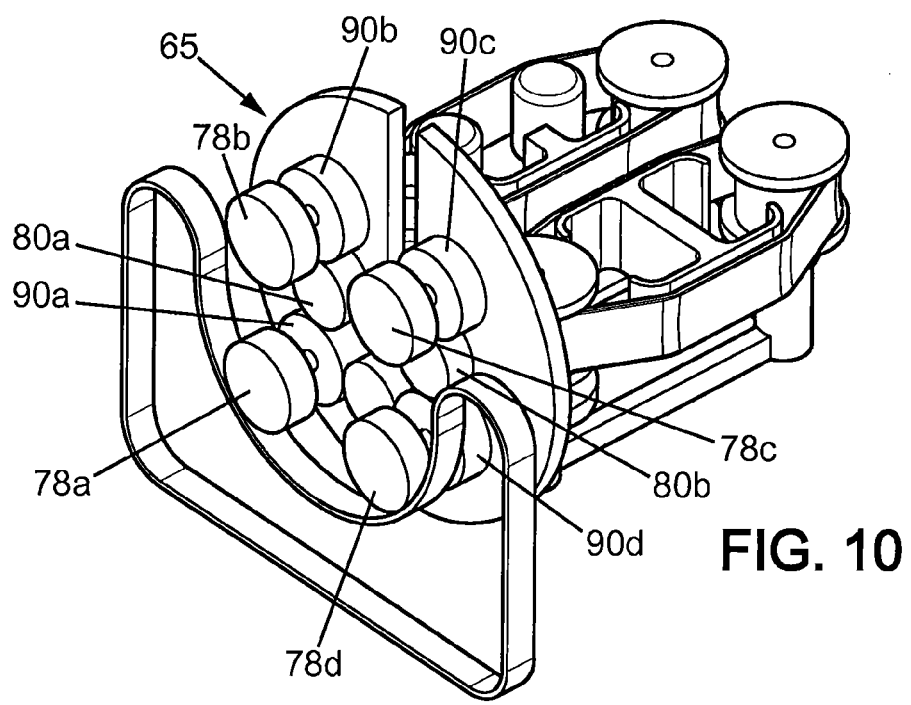
FIG. 10 is a view similar to FIG. 3 for a second embodiment.

We will now describe a second embodiment, with reference to FIG. 10. This embodiment is fairly similar to what was described above. It differs primarily in that the mechanized portion of the mobile part 65 of the transfer system 63 is implemented in two levels. A first level comprises gears 78a-78d having a meshing relation with the belt 66. A second level, parallel to the first and offset relative thereto in the main direction, comprises the head 79 of the shaft 44, and offset gears 90a-90d respectively corresponding to gears 78a-78d and connected to them, as well as intermediate gears 80a and 80b. This variant makes it easier to separate the driving portion of gears 78a-78d from the driving portion of the shaft 44.

An alternative embodiment will now be described in relation to FIG. 11. This embodiment still comprises a transfer system 63 comprising a fixed part 64 and a mobile part 65. In this embodiment, the fixed part is fairly simple, comprising two gears 91a, 91b, extending along axes parallel to each other and parallel to the main direction, and equidistant from axis 23, for example symmetrical relative to a plane of the base 21 passing through axis 23.

The mobile part 65 comprises a closed endless belt 92 that travels a path. The belt 92 may be guided as described above. The belt 92 comprises a first meshing portion 99, cooperating with the head 79 of the shaft 44. The belt has a driving portion 93 driven by the fixed part 64. The driving portion 93 comprises an arc portion 94 centered on the axis 23. The radius of the arc portion 94, the radius of the gears 91a and 91b, and the distance between the axis of the gears and the main axis 23, are chosen such that at least one gear 91a and 91b is in a meshing relation with the arc portion 94 of the belt 92. The central angle of the arc portion 94 of the belt 92 is chosen such that, regardless of the relative orientation of the movable element 22 relative to the base 21, at least one of the gears 91a and 91b is in a meshing relation with the arc portion 94 of the belt 92.

The belt 92 also comprises an access opening 95 aligned with the access opening 40 of the housing 39, together forming a single access opening 89. For this purpose, two guide pulleys 96a and 96b are provided that are supported by the housing 39 and are rotatable relative thereto about an axis parallel to the main direction, and around which the belt 92 is threaded. Thus, the belt comprises, in addition to the arc portion 94, an access opening portion 97 that is substantially U-shaped, of which the two arms 98a and 98b extend from a respective end of the arc portion 94 to a respective end of the meshing portion 99. The access opening 95 of the belt is defined between the two arms, through which the elongate flexible medical member 6 can be introduced in cooperation with belts 50 and 51. The maximum central angle of the arc portion 94 is defined to ensure an access opening 95 large enough to allow the passage of the elongate flexible medical member.

The example that has just been described functions as follows.

Figure 11:
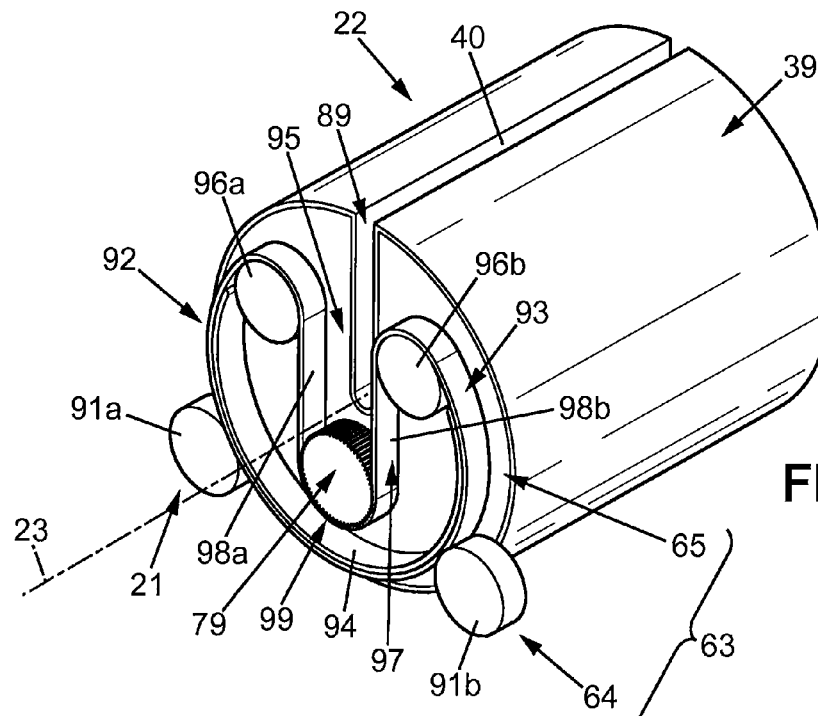
FIG. 11 is a view similar to FIG. 2 for a third embodiment.
Figure 11A:
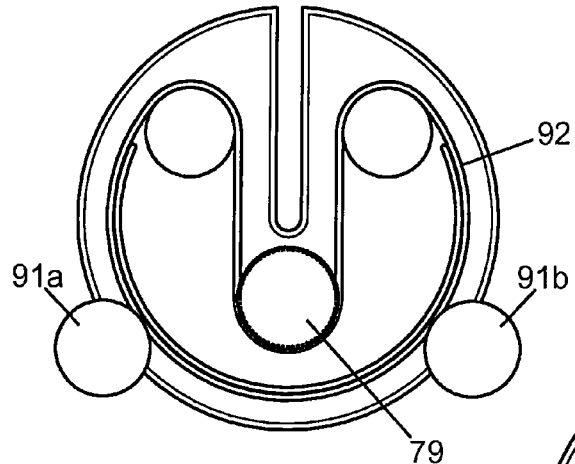
FIGS. 11a and 11b are front views of the system of FIG. 11 in different driving configurations.

In the initial position, as represented in FIGS. 11 and 11a, the elongate flexible medical member can be introduced in cooperation with belts 50 and 51, through the common access opening 89 formed by the access opening 40 of the housing and the access opening 95 of the belt 92.

For translational movement of the elongate flexible medical member 6, in the position of FIG. 11a, the rotation motor 19 is locked. Controlling the translation motor 20 generates rotation of gear 91a via a motion transfer system (not shown). In this example, the translation motor 20 may be engaged with the two gears 91a and 91b, where the two gears may be coupled to move jointly by either a mechanical or electronic connection system.

Rotation of gear 91a causes the belt 92 to move along its path, which causes the head 79 of the shaft 44 to rotate, and therefore the translation of the elongate flexible medical member. The elongate flexible medical member 6 can be withdrawn at any time.

Figure 11B:
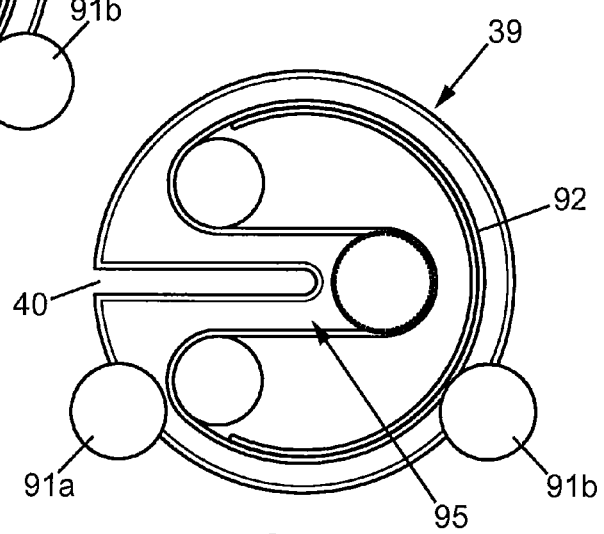

To rotate the elongate flexible member medical 6, one proceeds as in the first embodiment, by ordering the rotation of the rotation motor 19. This will cause the housing 39 to rotate, as represented in FIG. 11b. If generating translational movement of the elongate flexible medical member is not desired during this process, gears 91a and 91b can be coupled appropriately. Note that the elongate flexible medical member 6 can be removed at any time when in the position of FIG. 11b. If it is desired to generate a subsequent translational movement of the elongate flexible medical member in this position, one proceeds as described above. The elements are arranged such that the belt 92 is always in contact with at least one gear, here gear 91b, regardless of the orientation of the movable element 22 relative to the base 21.

Note that in an angular position where one of gears 91a and 91b (or any other element of the fixed part 64 that is not shown) is located within the axis of the common access opening 89, it is easy to order the rotation of the system, as described above, to a position where removal of the elongate flexible medical member is not prevented.

Figure 12:
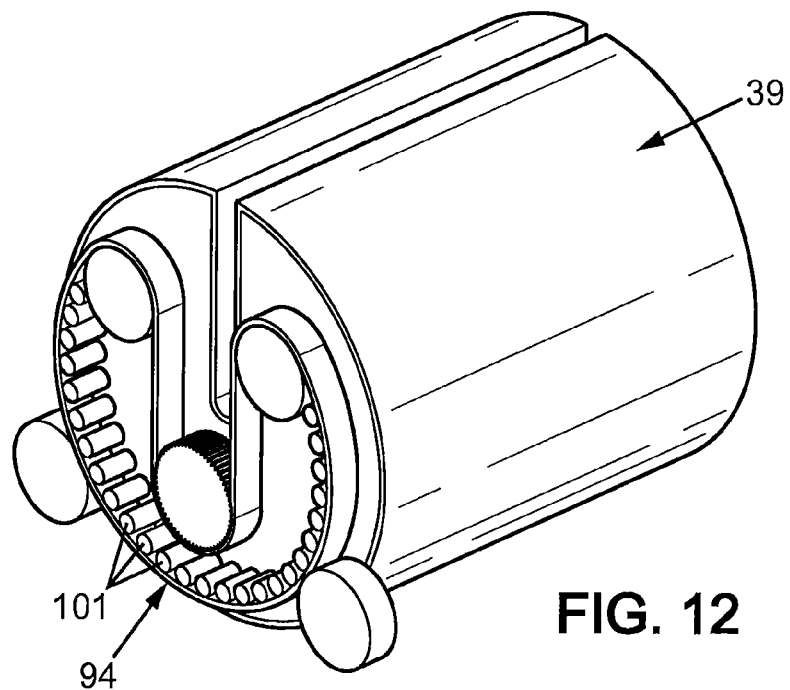
FIG. 12 is a view similar to FIG. 2 for a fourth embodiment.

To guide the belt 92 mounted on the housing 39, a guiding system may be used as described above in relation to FIG. 9. Alternatively, the housing 39 may support a plurality of rollers 101 parallel to each other and to the main direction and arranged along the inner surface of the arc portion 94, as represented in FIG. 12.

Figure 13:
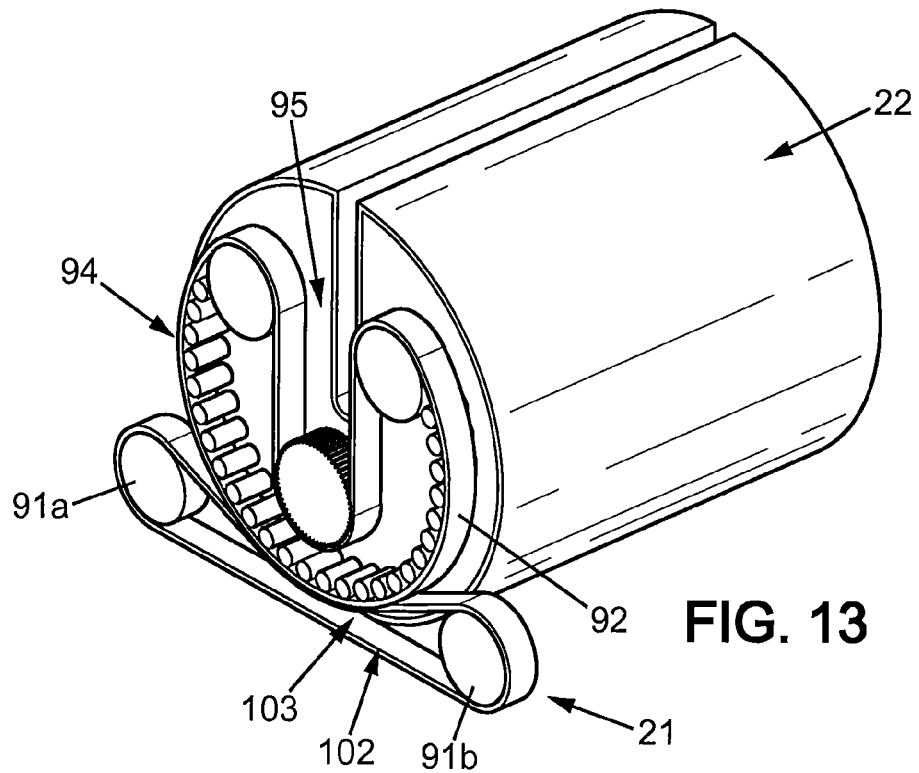
FIG. 13 is a view similar to FIG. 2 for a fifth embodiment.

As an alternative to having the two gears 91a and 91b in direct contact with the belt 92 mounted on the housing, according to an alternative embodiment illustrated in FIG. 13 it can be arranged so that the fixed part comprises two gears 91a and 91b, one driven by the translation motor 20, and a belt 102. The endless belt 102 is in a meshing relation with both gears 91a and 91b in order to transmit motion from one to the other. Moreover, the belt 102 comprises an arc portion 103 which cooperates with the arc portion 94 of belt 92. The cooperation between these two belts transmits a driving motion from one to the other. The central angle of the arc portion 103, centered on the main axis 23, of belt 102 is such that these two belts are in contact regardless of the relative orientation of the movable element 22 and the base 21. Thus, in the example shown, the central angle of the arc portion 103 of the belt 102 is at least greater than the central angle of the access opening 95 of the belt mounted on the housing. Moreover, to allow withdrawal of the elongate flexible medical member 6, the central angle of the arc portion 103 of belt 102 is less than 360° minus the central angle of the access opening 95 of the belt mounted on the housing.

Figure 14:
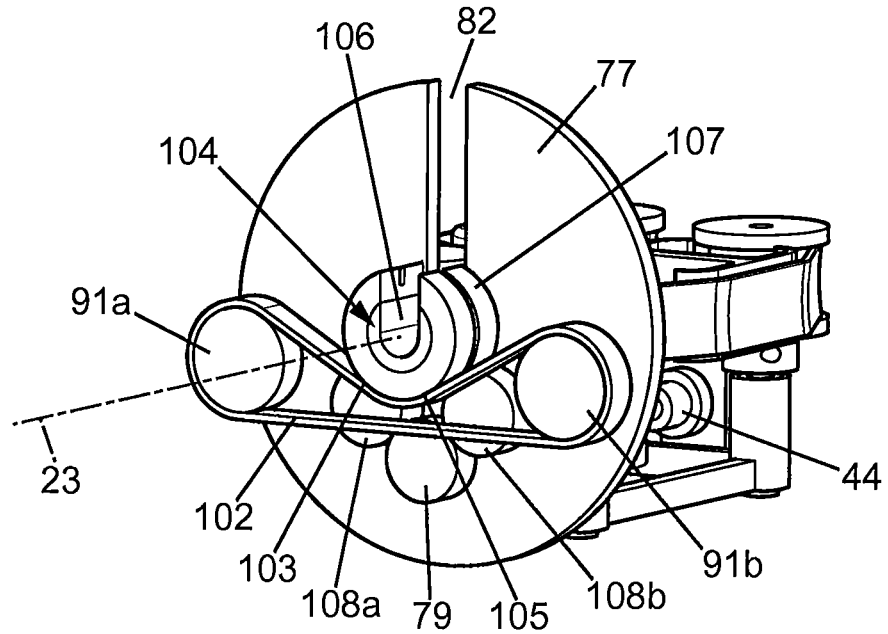
FIG. 14 is a view similar to FIG. 2 for a sixth embodiment.
Figure 14A:
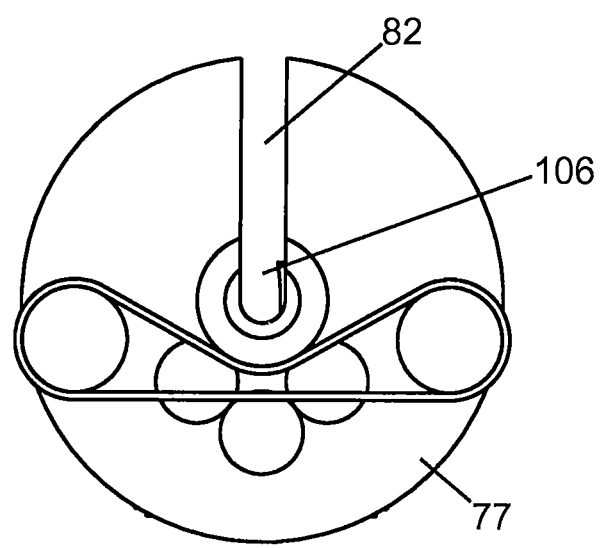
FIGS. 14a, 14b, and 14c are front views of the system of FIG. 14 in different driving configurations.
Figure 14B:
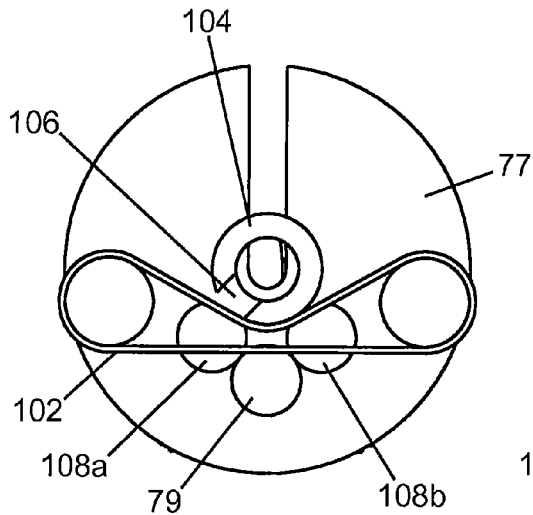
Figure 14C:
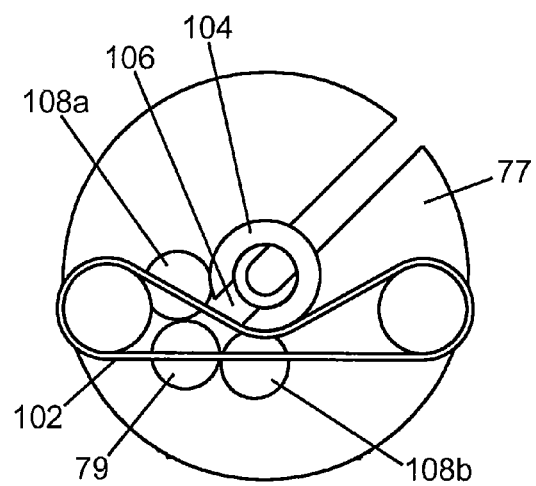

We will now describe another embodiment, with reference to FIGS. 14, 14a, and 14b. In this embodiment, the fixed part 64 comprises two gears 91a and 91b connected together by a belt 102, as in the example in FIG. 13. Unlike the above embodiment descriptions, this embodiment does not comprise a single access opening supported by the housing 39. Here, we have the housing 39 (represented by the support disc 77 with its access opening 82). However, the mechanized system comprises a slotted gear 104, carried by the support disc 77, mounted on the support disc 77 to be rotatable about the axis 23. This slotted gear 104 comprises a driving surface 105 cooperating with the arc portion 103 of the belt 102. It also comprises an access opening 106 having a central angle smaller than that of the arc portion 103 of the belt 102.

In this example, the mobile part 65 of the mechanized system of the transfer system 63 may be for example implemented in two levels, as described above for the embodiment of FIG. 10. The first level thus comprises gear 104.

The second level comprises a gear 107, connected to gear 104 and sharing its access opening with that gear, and the head 79 of the shaft 44. The second level further comprises a motion transfer system, transferring motion from gear 107 to the head 79 of the shaft 44. This transfer system comprises two identical gears 108a and 108b, each rotatable on the support disc 77 about the main direction, and arranged symmetrically to each other relative to a central plane passing through the center of the head 79 (axis of rotation of the shaft 44) and the center of gear 106 (axis 23). Each of gears 108a and 108b is in a meshing relation with both the head 79 and gear 107.

In particular, the gears are arranged so that, regardless of the orientation of gear 107 relative to the plate 77, the gear is in a meshing relation with at least one of gears 108a and 108b. However, each of gears 108a and 108b is constantly in a meshing relation with the head 79.

When the access opening 106 of gear 107 is directly in front of one of gears 108a and 108b, the other of these gears is in a meshing relation with gear 107, ensuring the transfer of motion to the shaft 44.

The embodiment which has just been described functions as follows. In a rest position as shown in FIG. 14a, the two access openings 106 and 82 coincide, such that the elongate flexible medical member 6 can be installed between belts 50 and 51.

To drive the elongate flexible medical member in translation along axis 23, the user prevents rotation and controls the translation motor 20 as described above, driving the belt 102 of the fixed part. The movement of the belt 102 causes gear 104 to rotate about axis 23, which in turn causes rotation of the shaft 44 via one and/or the other of the intermediate gears 108a and 108b.

As can be seen in FIG. 14b (disregarding the rotation of the support disc 77), when the access opening 106 of gear 104 is facing intermediate gear 108a, motion is smoothly transmitted via intermediate gear 108b (and vice versa).

To drive the elongate flexible medical member 6 in rotation, the rotation motor 19 is controlled to generate rotation of the housing (joined to the support disc 77). If translational movement of the elongate flexible medical member is not to be generated during this operation, one can simultaneously control the translation motor to drive the belt in a manner that provides rigid rotation of the shaft 44 about the main direction without rotation of the shaft 44 relative to the support disc 77.

Thus, in one aspect embodied in the above examples, the invention relates to a robotic module for driving a catheterization system, comprising a base and a movable element that is mounted to be rotatable, relative to the base, about an axis of rotation extending in a main direction. In this aspect, the movable element comprises:

a mounting extending between first and second ends along the axis of rotation, the mounting having a surface for driving rotation about said axis, the mounting comprising an access opening extending between its first and second ends along the axis of rotation.

The movable element also comprises a translation control gear, supported by the mounting and rotatable relative to the mounting about an axis extending in said main direction, which when driven generates a translational movement of the elongate flexible medical member in the main direction.

The movable element comprises a transfer system comprising a fixed part supported by the base and a mobile part supported by the mounting, the fixed part being drivable by a motor member integral to the base, the mobile part being operatively coupled to the translation control gear such that the translation control gear is in a driving relation with the mobile part, the mobile part having an access opening.

First and second parts are selected among the fixed part and the mobile part, and the first part comprises at least one closed flexible belt having a partially circular path about the axis of rotation, arranged so that, regardless of the relative orientation of the base and the mounting about the main direction, at least a portion of said belt in said path is in an engaging relation with the second part, in order to transmit motion from the motor member to the translation control gear.

Figure 15:
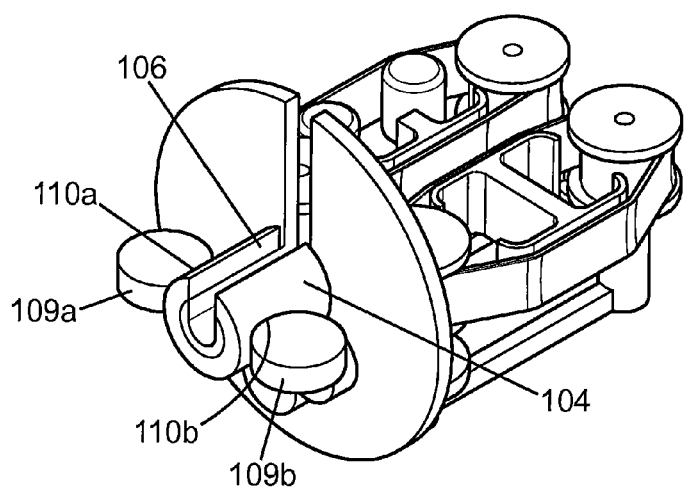
FIG. 15 is a view similar to FIG. 2 for a seventh embodiment.

FIG. 15 describes another embodiment of the invention. This embodiment is similar to that of FIG. 14. The main difference is in the fixed part of the transfer system. Here it comprises two gears 109a and 109b. These are directly controlled by the translation motor, or are connected to one another. They are arranged symmetrically to each other relative to a central plane passing through axis 23 and the axis of the head 79 of the shaft 44. Each comprises a driving portion, respectively 110a and 110b, which cooperates with the gear 104 of the mobile part of the transfer system. Thus, if the access opening 106 of gear 104 is facing one of the gears of the fixed part, for example gear 109a, the transfer of translational motion to the elongate flexible medical member 6 via the other gear 109b, and vice versa, is ensured.

Thus, in one aspect as implemented in all the above embodiments except the one of FIG. 13, the invention relates to a robotic module for driving a catheterization system, comprising a base and a movable element that is mounted to be rotatable, relative to the base, about an axis of rotation extending in the main direction.

In this aspect, the movable element comprises a mounting extending between first and second ends along the axis of rotation, the mounting having a surface for driving rotation about said axis, said mounting comprising an access opening extending between its first and second ends along the axis of rotation.

The movable element also comprises a translation control gear, supported by the mounting and rotatable relative to the mounting about an axis extending in said main direction, which when driven generates a translational movement of the elongate flexible medical member in the main direction.

The movable element also comprises a transfer system comprising a fixed part supported by the base and a mobile part supported by the mounting, the fixed part being drivable by a motor member integral to the base, the mobile part being operatively coupled to the translation control gear such that the translation control gear is in a driving relation with the mobile part.

First and second parts are selected among the fixed part and the mobile part. The first part comprises at least two members arranged so that, regardless of the relative orientation of the base and the mounting about the main direction, at least one of said members is in an engaging relation with the second part, in order to transmit motion from the motor member to the translation control gear.

The invention claimed is:

1. A robotic module for driving a catheterization system, comprising a base and a movable element mounted to be rotatable, relative to the base, about an axis of rotation extending in a main direction, the movable element comprising:

a mounting extending between first and second ends along the axis of rotation, the mounting having a surface for driving rotation about said axis, said surface for driving rotation comprising an access opening extending in the main direction, a translation control gear, supported by the mounting and rotatable relative to the mounting about an axis extending in said main direction, which when driven generates a translational movement of an elongate flexible medical member along the main direction, and a transfer system comprising a fixed part supported by the base and a mobile part supported by the mounting, the fixed part and the mobile part being in a driving relation, the fixed part being drivable by a motor member integral to the base, the mobile part being operatively coupled to the translation control gear such that the translation control gear is in a driving relation with the mobile part, the mobile part having an access opening, wherein the access opening of the mobile part extends as a continuity of the access opening of the surface for driving rotation in the main direction, regardless of the relative orientation of the mounting and the base about the axis of rotation.

2. The driving module according to claim 1, wherein the mobile part comprises a plurality of gears which are in a meshing relation with each other and with the translation control gear and, regardless of the relative orientation of the mounting and the base, at least one of said gears of the mobile part is in a driving relation with the fixed part.

3. The driving module according to claim 1, wherein the mobile part comprises a belt supported by the mounting and following a path that defines the access opening of the mobile part.

4. The driving module according to claim 1, wherein first and second parts are selected among the fixed part and the mobile part, and wherein the first part comprises at least one closed flexible belt having a partially circular path about the axis of rotation, arranged so that, regardless of the relative orientation of the base and the mounting about the main direction, at least a portion of said belt in said path is in an engaging relation with the second part, in order to transmit motion from the motor member to the translation control gear.

5. The driving module according to claim 1, wherein first and second parts are selected among the fixed part and the mobile part, and wherein the first part comprises at least two members arranged so that, regardless of the relative orientation of the base and the mounting about the main direction, at least one of said members is in an engaging relation with the second part, in order to transmit motion from the motor member to the translation control gear.

6. The module according to claim 5, wherein the first part is the fixed part, and wherein the two members are synchronized.

7. The module according to claim 5, wherein the first part is the fixed part, and wherein the mobile part further comprises at least two members arranged so that, regardless of the relative orientation of the base and the mounting about the main direction, at least one of said members is in an engaging relation with the translation control gear, in order to transmit motion from the motor member to the translation control gear.

8. The module according to claim 5, wherein the first part is the mobile part, and wherein two members are in a meshing relation with the translation control gear.

9. The module according to claim 8, wherein one of the two members is in an indirect meshing relation with the translation control gear via an intermediate gear.

10. The module according to claim 9, wherein one of the two members is in an indirect meshing relation with the translation control gear via the other of the two members.

11. The module according to claim 8, wherein the mobile part further comprises at least a third member in a meshing relation with the translation control gear and with the fixed part.

12. The module according to claim 5, wherein the fixed part comprises a closed endless belt comprising a portion following a circular path centered on said axis of rotation.

13. The module according to claim 12, comprising at least first and second parallel covers, each comprising a groove, the grooves of the first and second covers facing one another, said grooves guiding the belt.

14. The module according to claim 12, wherein the belt is supported by the base.

15. The module according to claim 12, wherein the belt is supported by the mounting.

16. The module according to claim 15, wherein the mounting supports a plurality of rollers that are rotatable relative to the mounting about the main direction, and that guide the belt.

17. The robotic module for driving a catheterization system, comprising a base and a movable element mounted to be rotatable, relative to the base, about an axis of rotation extending in a main direction, the movable element comprising:
  a mounting extending between first and second ends along the axis of rotation, the mounting having a surface for driving rotation about said axis, said mounting having an access opening extending between its first and second ends along the axis of rotation,
  a translation control gear, supported by the mounting and rotatable relative to the mounting about an axis extending in said main direction, which when driven generates a translational movement of an elongate flexible medical member along the main direction, and
  the driving module comprising a transfer system comprising a fixed part supported by the base and a mobile part supported by the mounting, the fixed part being drivable by a motor member integral to the base, the mobile part being operatively coupled to the translation control gear such that the translation control gear is in a driving relation with the mobile part, the mobile part having an access opening,
  wherein that first and second parts are selected among the fixed part and the mobile part, and in that the first part comprises at least one closed flexible belt having a partially circular path about the axis of rotation, arranged so that, regardless of the relative orientation of the base and the mounting about the main direction, at least a portion of said belt in said path is in an engaging relation with the second part, in order to transmit motion from the motor member to the translation control gear.

18. The module according to claim 17, wherein the mobile part has an access opening.

19. The module according to claim 18, wherein the access opening of the mobile part and the access opening of the mounting are joined together, regardless of the relative orientation of the base and the mounting about the main direction.

20. A robotic module for driving a catheterization system, comprising a base and a movable element mounted to be rotatable, relative to the base, about an axis of rotation extending in a main direction,
  the movable element comprising a mounting extending between first and second ends along the axis of rotation, the mounting having a surface for driving rotation about said axis, said mounting comprising an access opening extending between its first and second ends along the axis of rotation,
  the movable element further comprising a translation control gear, supported by the mounting and rotatable relative to the mounting about an axis extending in said main direction, which when driven generates a translational movement of an elongate flexible medical member along the main direction,
  the driving module comprising a transfer system comprising a fixed part supported by the base and a mobile part supported by the mounting, the fixed part being drivable by a motor member integral to the base, the mobile part being operatively coupled to the translation control gear such that the translation control gear is in a driving relation with the mobile part, and
  first and second parts being selected among the fixed part and the mobile part, the first part comprising at least two members arranged so that, regardless of the relative orientation of the base and the mounting about the main direction, at least one of said members is in an engaging relation with the second part, in order to transmit motion from the motor member to the translation control gear.

* * * * *